(12) United States Patent
Waagen et al.

(10) Patent No.: US 10,791,913 B2
(45) Date of Patent: Oct. 6, 2020

(54) PRESSURE RELIEF VENT FOR SEALED INSTRUMENTS

(71) Applicant: KARL STORZ Endovision, Inc., Charlton, MA (US)

(72) Inventors: Tyrel Waagen, Sturbridge, MA (US); Jeffrey Melanson, Sturbridge, MA (US)

(73) Assignee: KARL STORZ Endovision, Inc., Charlton, MA (US)

( * ) Notice: Subject to any disclaimer, the term of this patent is extended or adjusted under 35 U.S.C. 154(b) by 0 days.

(21) Appl. No.: 16/414,384

(22) Filed: May 16, 2019

(65) Prior Publication Data

US 2019/0269305 A1    Sep. 5, 2019

Related U.S. Application Data

(62) Division of application No. 14/979,619, filed on Dec. 28, 2015, now Pat. No. 10,335,017.

(51) Int. Cl.

| F16K 17/00 | (2006.01) |
| F16K 17/04 | (2006.01) |
| F16K 24/00 | (2006.01) |
| A61B 1/00 | (2006.01) |
| A61B 1/012 | (2006.01) |

(52) U.S. Cl.
CPC ...... *A61B 1/00137* (2013.01); *A61B 1/00066* (2013.01); *A61B 1/00121* (2013.01); *A61B 1/00135* (2013.01); *A61B 1/012* (2013.01)

(58) Field of Classification Search
CPC .... F16K 17/168; F16K 17/0486; F16K 17/00; F16K 17/003; F16K 17/02; F16K 17/04; F16K 24/00

USPC ........ 137/535, 538, 540; 73/1.17, 49.8, 45.5
See application file for complete search history.

(56) References Cited

U.S. PATENT DOCUMENTS

| 4,878,484 A | ‡ | 11/1989 | Miyagi ................. | A61B 1/121 600/13 |
| 5,547,456 A | ‡ | 8/1996 | Strobl .................... | A61B 1/121 600/12 |
| 5,662,139 A | * | 9/1997 | Lish ........................ | A62C 37/50 137/523 |
| 5,807,238 A | ‡ | 9/1998 | Feldman ............ | A61B 1/00057 600/13 |

(Continued)

*Primary Examiner* — Paul J Gray
(74) *Attorney, Agent, or Firm* — The Culbertson Group, P.C.; Michael Loi (57) ABSTRACT

A pressure control and leak test system for a medical instrument includes an upper housing, a valve member, and a vent opening arrangement. The upper housing includes a cavity for fluid communication with an interior of the medical instrument and an aperture in fluid communication with the cavity. The valve member includes a stem within the aperture and a cap section. The cap section includes a proximal-facing end with a bottom surface and a distal-facing end. The vent opening arrangement includes a first feature of the cap section and a second feature on the distal end of the upper housing. The valve member rotates relative to the housing causing the first feature and the second feature to seal the cap section with the housing in a first position and separate the cap section from the housing in a second position.

18 Claims, 8 Drawing Sheets

(56) References Cited

U.S. PATENT DOCUMENTS

| | | | | |
|---|---|---|---|---|
| 5,868,667 A ‡ | 2/1999 | Lin | ........................ | A61B 1/121 |
| | | | | 600/12 |
| 6,942,195 B2 * | 9/2005 | Kao | ...................... | E03C 1/0404 |
| | | | | 251/230 |
| 2013/0228241 A1 * | 9/2013 | Gass | ........................ | E03B 7/078 |
| | | | | 137/512 |
| 2014/0100425 A1 ‡ | 4/2014 | Metras | ............... | A61B 1/00137 |
| | | | | 600/15 |

\* cited by examiner
‡ imported from a related application

PRESSURE RELIEF VENT FOR SEALED INSTRUMENTS

TECHNICAL FIELD OF THE INVENTION

The invention relates to sealed instruments such as endoscopes and to pressure relief vents which may be employed with sealed instruments. Pressure relief vents according to the invention maintain the desired seal for the instrument during normal operation of the instrument, but also allow pressure relief to protect the instrument from potentially damaging pressure differentials.

BACKGROUND OF THE INVENTION

Instruments such as endoscopes define an interior volume which is sealed during normal operation in order to, among other things, protect sensitive internal components of the instrument. Maintaining a seal to the interior volume during normal operation of the instrument also simplifies cleaning and sterilizing the instrument after use.

Although the instrument remains sealed in normal operation, there are circumstances in which it is desirable to temporarily break the seal to the interior volume. For example, in the case of air transport it is desirable to break the seal to the interior volume of the instrument in order to prevent a potentially damaging positive pressure differential between the interior volume of the instrument and the relatively lower pressure of the atmosphere inside the aircraft at high altitude. A positive pressure differential applied to an endoscope, for example, may cause elastic expansion in flexible sheathing material associated with the probe of the instrument. This expansion may result in elastic fatigue which eventually damages the material and may ultimately cause the material to rupture.

In the case of cleaning or sterilization, a sealed instrument may be subjected to conditions which produce both positive and negative pressure differentials between the interior volume of the instrument and the atmosphere in which the instrument is located. Positive pressure differentials during cleaning or sterilization pose the same threat noted above in relation to air transport. Negative pressure differentials may also damage certain components of the instrument.

Sealed instruments may also be subjected to testing which produces pressure differentials between the instrument interior volume and the surrounding atmosphere. An endoscope, for example, may be tested for leaks by opening a port in the endoscope body to apply a small positive pressure to the interior volume of the instrument, and then submerging the instrument in a liquid. Any leak in the instrument is apparent as the gas in the interior volume escapes through the leak and forms bubbles in the liquid.

In the field of endoscopes, it is known to take measures to avoid potentially damaging pressure differentials and thereby avoid damage which may be caused by such differentials. U.S. Pat. No. 5,807,238 shows a sterilization cap which is attached to an endoscope prior to subjecting the instrument to a sterilization process. The sterilization cap is adapted to attach to a sealed port on the endoscope, the port being sealed by a valve which remains closed during normal operation of the instrument. The sterilization cap disclosed in U.S. Pat. No. 5,807,238 includes two separate check valves, and is adapted to open the valve of the sealed port as the cap is attached. One check valve is configured to open in response to a predetermined positive pressure differential between the interior volume of the instrument and the surrounding atmosphere, while the other check valve is configured to open in response to a predetermined negative pressure differential between the interior volume of the instrument and the surrounding atmosphere. U.S. Pat. No. 5,807,238 also discloses using a filter or membrane in the sterilization cap in order to prevent sterilizing liquids from reaching the interior volume of the instrument while still allowing gasses to pass into and out of the interior volume of the instrument when the sterilization cap is installed.

A problem with the arrangement shown in U.S. Pat. No. 5,807,238 is that the sterilization cap must be manually attached to a normally closed/sealed port of the endoscope in order to facilitate the desired pressure relief. Should the sterilization cap be connected incorrectly to the instrument or not installed at all prior to air transport or a sterilization procedure, the instrument remains sealed and may be damaged by positive or negative pressure differentials which may arise.

SUMMARY OF THE INVENTION

It is an object of the invention to provide a pressure relief vent which overcomes the above-described problems and others associated with sealed instruments such as endoscopes. The invention encompasses a pressure relief vent which can be installed on an open port of a sealed instrument such as an endoscope and remain continuously installed on the instrument not only for normal operation but also for transport, testing, and cleaning/sterilization. The invention also encompasses a sealed instrument such as an endoscope including a pressure relief vent which remains continuously operational both during normal operation of the instrument and otherwise to automatically prevent potentially damaging pressure differentials.

A pressure control and leak test system for a medical instrument includes and upper housing, a valve member, and a vent opening arrangement. The upper housing includes a proximal end forming a cavity for fluid communication with an interior of the medical instrument and an aperture in fluid communication with the cavity through a distal end of the upper housing. The valve member includes a proximal end including a stem within the aperture and a distal end including a cap section. The cap section includes a proximal-facing end with a bottom surface and a distal-facing end. The vent opening arrangement includes a first feature on the bottom surface of the cap section and a second feature on the distal end of the upper housing. The first feature is in rotatable engagement with the second feature. The valve member rotates relative to the housing causing the first feature and the second feature to seal the cap section with the housing in a first position and separate the cap section from the housing in a second position.

In other features, a distal end of the aperture is blocked in the first position and at least partially open in the second position to allow fluid flow from the cavity through the aperture to between the cap section and the housing.

In other features, the first feature includes an arcuate element and the second feature includes a ridge. The arcuate element further comprises a ramp projecting away from the bottom surface of the cap to engage with the ridge. The ramp is at least partially engaged with the ridge in the second position and disengaged from the ridge in the first position. An arcuate recess receives the arcuate element in the first position. A stop section at one end of the arcuate element prevents the cap section from further rotation.

In other features, at least one receiver is formed in the distal-facing end of the cap section. A leak test fitting including at least one projection engages the at least one receiver in the distal-facing end of the cap section to rotate the cap section relative to the housing. The leak test fitting includes a fitting passage blocked from fluid communication with the aperture in the first position and in fluid communication with the aperture in the second position. Locking features on the upper housing lock the leak test fitting to the upper housing in the second position. The locking features comprise gaps and a locking ridge of the leak test fitting aligns with the gaps to allow the leak test fitting to engage the upper housing when the valve member is in the first position and engage the locking features when the valve member is in the second position to lock the leak test fitting to the upper housing.

In other features, a biasing device engaged with the upper housing and the valve member biases the cap section to the first position. The biasing device includes a biasing force configured to allow the cap section to move to the second position when a pressure differential between the cavity and atmospheric pressure exceeds a predetermined threshold.

In other features, a seal is disposed between the bottom surface of the cap section and a groove in the distal end of the upper housing. A seal is disposed within a vent receiving cavity of the leak test fitting.

In other features, a threaded section on the proximal end of the upper housing couples to the medical instrument. A threaded section on the proximal end of the upper housing couples to a housing base. In other features, a connector on a proximal end of the housing base couples with the medical instrument.

These and other advantages and features of the invention will be apparent from the following description of illustrative embodiments, considered along with the accompanying drawings.

DESCRIPTION OF ILLUSTRATIVE EMBODIMENTS

Figure 1:
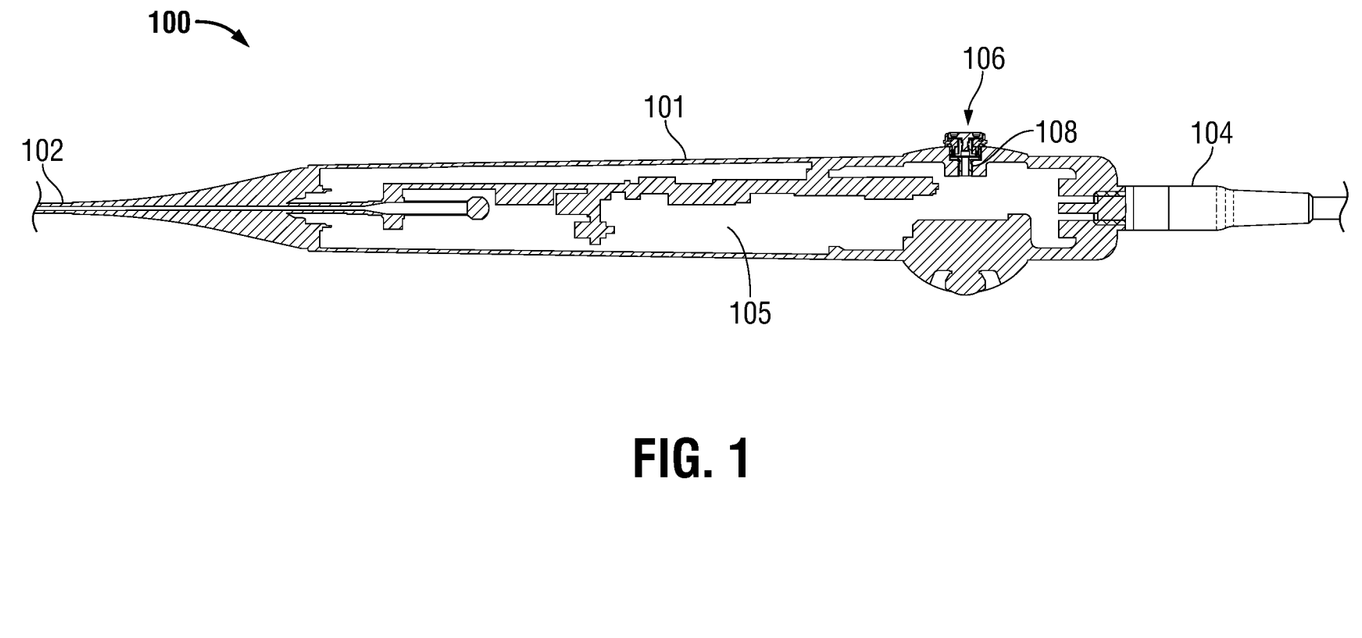
FIG. 1 is a partial longitudinal section view of a sealed instrument according to an embodiment of the present invention.

Referring to FIG. 1, an example sealed instrument comprises an endoscope 100 having an instrument body 101 formed from a suitable rigid material such as stainless steel. Endoscope 100 includes a probe 102 connected at a first end of instrument body 101 and a connector 104 at the opposite end of the instrument body. Only a small portion of probe 102 is shown in FIG. 1, however, it will be appreciated by those skilled in the art that the probe includes an elongated sheathed element that extends to a distal end. Connector 104 provides an interface with the instrument body through which data and control signals may be sent to and from components housed within instrument body 101 or probe 102.

FIG. 1 shows that instrument body 101 defines an interior volume 105 within which various electrical, optical, and mechanical components of the endoscope may be housed. In normal operation of endoscope 100, interior volume 105 is sealed from the surrounding atmosphere by instrument body 101. Because interior volume 105 is sealed from the surrounding atmosphere, changes in atmospheric pressure produce pressure differentials between the pressure in interior volume 105 and the atmosphere. In order to prevent potentially damaging pressure differentials from occurring between the interior volume 105 and the atmosphere in which the instrument is located, endoscope 100 includes a pressure relief vent 106 mounted at a port 108 formed in instrument body 101. Pressure relief vent 106 may be connected at port 108 through any suitable connection such as a suitable threaded connection. As will be described further below, embodiments of pressure relief vent 106 may provide pressure relief in response to a predefined positive pressure differential between interior volume 105 and the surrounding atmosphere or in response to either one of a predefined positive pressure differential or predefined negative pressure differential.

Figure 2:
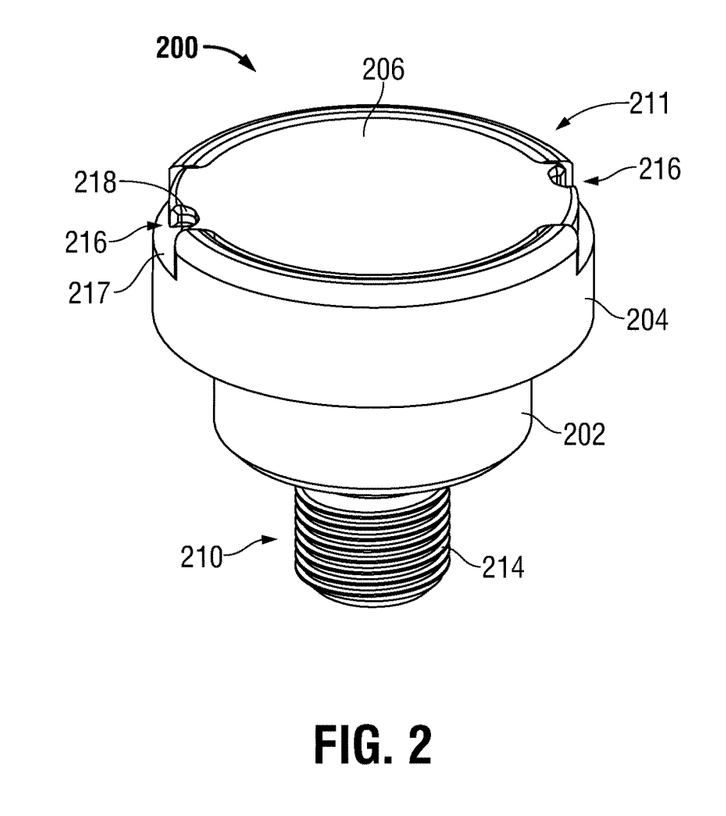
FIG. 2 is a perspective view of a pressure relief vent according to an embodiment of the present invention
Figure 3:
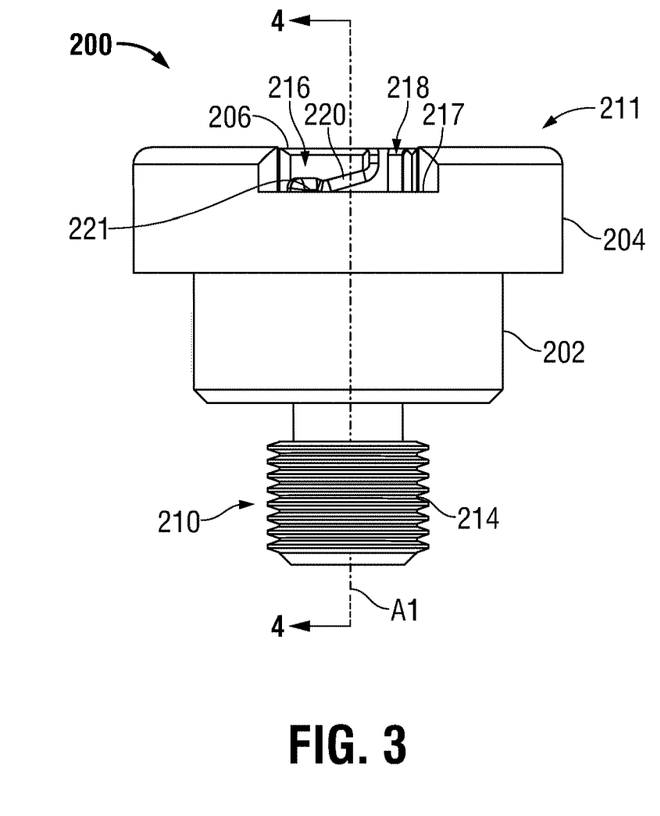
FIG. 3 is a side view of the pressure relief vent shown in FIG. 2.

FIGS. 2 and 3 show a pressure relief vent 200 according to one embodiment of the present invention which may be used as the pressure relief vent 106 in FIG. 1. Pressure relief vent 200 includes a housing base 202, an upper housing 204 and a valve member of which only a cap section 206 is visible in FIGS. 2 and 3. These elements, the housing base 202, upper housing 204, and valve member (which will be described further in connection with the section view of FIG. 4), define a vent enclosure of pressure relief vent 200 having a vent enclosure axis A1 shown in FIG. 3. This vent enclosure includes a proximal end shown generally at reference numeral 210 and a distal end shown generally at reference numeral 211. Valve member cap section 206, which is generally disc-shaped in this embodiment, is located generally at the distal end 211, while a connector 214 for the pressure relief vent is located at proximal end 210.

Also visible in FIGS. 2 and 3 are two vent opening devices each shown generally at reference numeral 216. In this particular embodiment, each vent opening device 216 includes a cutout in upper housing 204 with a bottom surface 217 and an entry slot 218. Entry slot 218 is formed at an edge of valve member cap section 206. Vent opening device 216 also includes a ramp section 220 and end part 221 shown only in FIG. 3. The operation of vent opening device 216 will be described below in connection with FIGS. 4 through 7.

Figure 4:
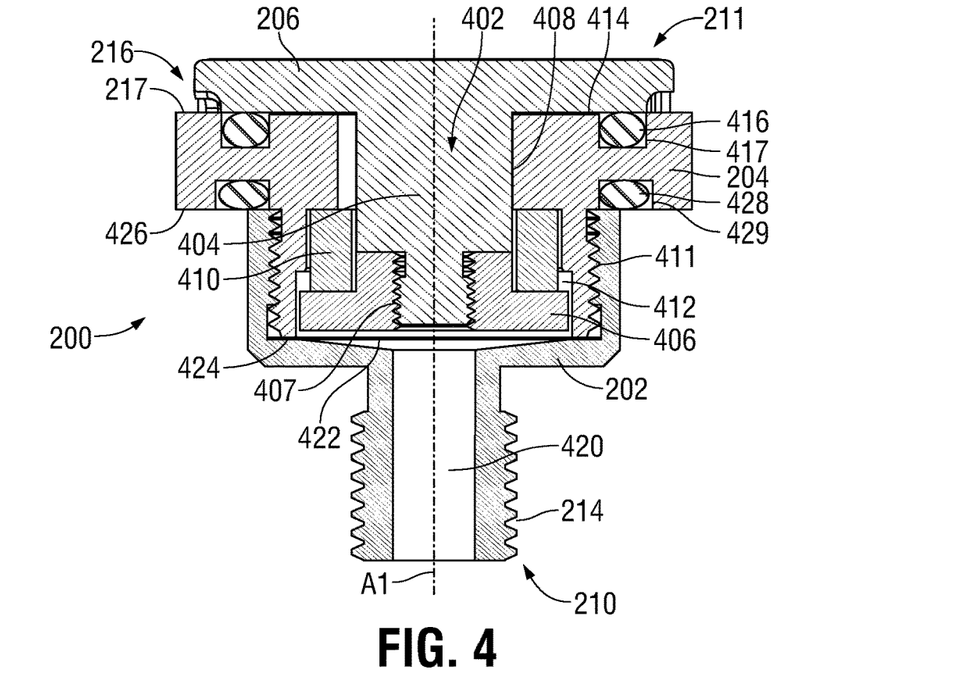
FIG. 4 is a view in section taken along line 4-4 in FIG. 3.

The section view of FIG. 4 shows the valve member 402. Valve member 402 includes a stem section 404 and a bottom plate 406 in addition to the cap section 206 visible in FIGS. 2 and 3. Bottom plate 406 is removably connected to the rest of valve member 402 through a threaded connection 407 in this embodiment. This removable connection allows the stem section 404 (which may be cylindrically shaped in this embodiment) to be inserted through an aperture 408 of upper housing 204 to a position in which bottom plate 406 may be connected with a biasing device 410 captured between bottom plate 406 and upper housing 204. With the bottom plate 406 connected and biasing device 410 captured, housing base 202 may then be connected to upper housing 204 through a threaded connection 411 so as to position both bottom plate 406 and biasing device 410 within a cavity 412 of the vent enclosure.

In the position shown in FIG. 4, biasing device 410, which may comprise a wave spring or any other suitable biasing element, is operable to bias valve member 402 downwardly in the orientation of the figure. This bias forces the bottom surface 414 of the cap section 206 toward a top surface of upper housing 204 and in particular toward an O-ring 416 positioned in a groove 417 in the upper surface of upper housing 204. Contact between cap section bottom surface 414 and O-ring 416 produces a seal along the top of O-ring 416. This seal at O-ring 416 isolates the interior volume of the vent enclosure (in this case made up of the space between aperture 408 and stem section 404, open space remaining in the upper housing cavity 412, and a passage 420 through housing base 202) from the atmosphere when pressure relief valve 200 is connected to a sealed instrument via connector 214.

Pressure relief vent 200 shown in FIG. 4 also includes a gas permeable membrane 422 captured between housing base 202 and a bottom end 424 of upper housing 204. As will be described further below, membrane 422 allows gases to pass there through but blocks liquids which may inadvertently enter pressure relief vent 200 when the vent is in an open condition.

Although the embodiment shown in FIG. 4 employs a threaded connection 407 between the stem section 404 and bottom plate 406 of valve member 402, it should be noted that embodiments of the invention are not limited to such a removable connection between the bottom plate and the rest of the valve member. In embodiments having a biasing device capture arrangement such as that shown in FIG. 4, it is only desirable that the bottom plate initially be separate from the rest of the valve member so that the two separate pieces can be connected in some fashion to capture the biasing device in the position of biasing device 410 shown in FIG. 4. For example, rather than a threaded connection between bottom plate 406 and the rest of the valve member 402, the bottom plate may be adapted to be welded or otherwise irremovably connected to the rest of the valve member once the valve member 402, upper housing 204, and biasing device 410 are arranged in the relative positions shown in FIG. 4. Where a threaded connection such as connection 407 is employed, it is desirable to make the connection with a suitable locking compound to help prevent bottom plate 406 from becoming separated inadvertently during use of the pressure relief vent.

The assembled pressure relief vent 200 shown in FIG. 4 may be connected to an instrument such as endoscope 100 shown in FIG. 1 by threading connector 214 into a cooperating thread associated with port 108 shown in FIG. 1. Port 108 may be configured such that the entire housing base 202 is received in a cavity defining the port, and a lower surface 426 of upper housing 204 rests against an outer surface of the instrument body. O-ring 428 in groove 429 shown in FIG. 4 may help provide a seal between upper housing 204 and housing base 202 and also between the pressure relief vent 200 and instrument body (such as instrument body 101 in FIG. 1). In any event, it will be appreciated that when pressure relief vent 200 is operatively connected to an instrument via connector 214 shown in FIGS. 2 through 4, the interior volume of the instrument is connected and open to the interior volume of the pressure relief vent through passage 420.

Figure 5:
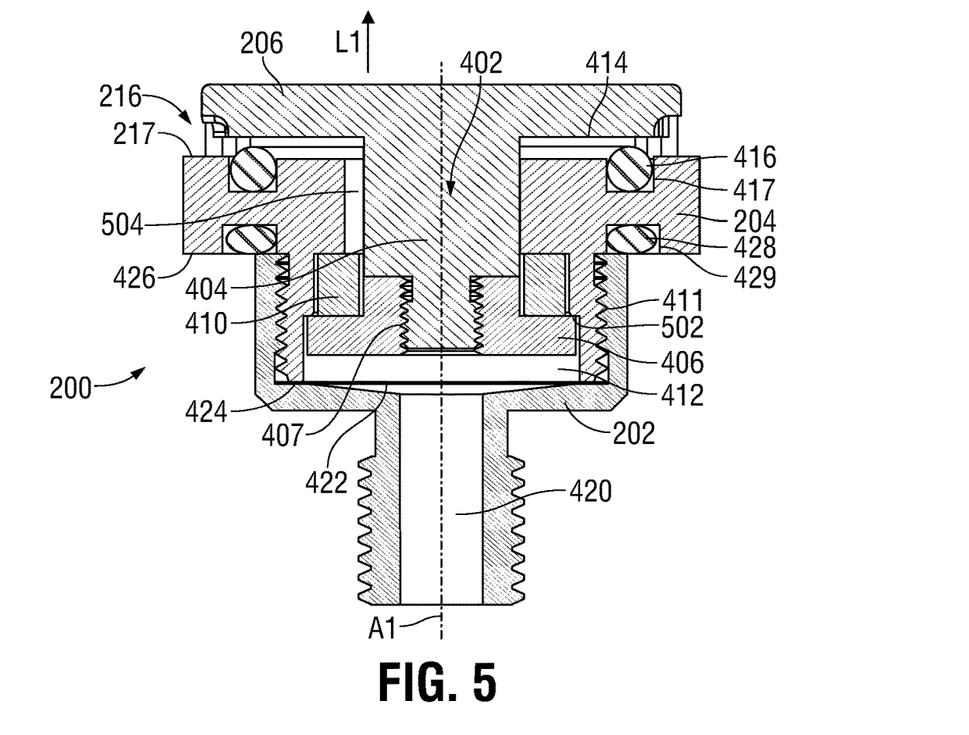
FIG. 5 is a view in section similar to FIG. 4, but showing the pressure relief vent in an open condition.

The operation of pressure relief vent 200 to provide relief from an undesirable positive pressure differential between an interior volume of an instrument and an atmosphere in which the instrument and the pressure relief vent are located can now be described with particular reference to FIGS. 4 and 5. With pressure relief vent 200 operatively connected to an instrument as described above, the pressure within the interior volume of the instrument is applied through housing base/connector passage 420 to the interior volume of the pressure relief vent defined by housing base 202, upper housing 204, and valve member 402. When a predefined positive pressure differential is reached, the force applied to valve member 402 in the direction L1 in FIG. 5 is sufficient to overcome the biasing force of biasing device 410 and lift valve member 402 in the direction L1. Although movement in the direction L1 is limited in this embodiment by contact between bottom plate 406 and upper housing 205 at stop feature 502 shown in FIG. 5, this movement of valve member 402 in direction L1 is sufficient to break the seal between surface 414 and O-ring 416 as shown in FIG. 5 and allows gases within the interior volume of pressure relief vent 200 to flow through the gap formed between bottom surface 414 and the O-ring 416 and to the atmosphere. One or more channels 504 may be included through upper housing 204 to help enhance the flow of gas from the vent enclosure interior volume under a given pressure differential. Gas continues to be released until the pressure differential is no longer sufficient to overcome the biasing force of biasing device 410, at which point valve member 402 returns to the position shown in FIG. 4 to reestablish the seal for pressure relief vent 200 (the seal between O-ring 416 and surface 414 in this embodiment).

The combination of valve member 402 which is movable relative to upper housing 204 and biasing device 410 acting between lower plate 406 and upper housing 204 represents a pressure relief arrangement in the embodiment of FIGS. 2 through 5. The closed condition of this pressure relief arrangement is shown in FIG. 4 and the open condition of the pressure relief arrangement is shown in FIG. 5. In the closed condition, biasing device 410 is in a relatively relaxed, expanded state. However, as valve member is raised to the open condition shown in FIG. 5, biasing device 410 moves to a compressed state.

As noted above in connection with FIGS. 2 and 3, pressure relief vent 200 also includes vent opening devices 216. These vent opening devices are operable to move the pressure relief arrangement from the closed to open condition in response to a manual operation applied at the distal end of the vent enclosure. Such an operation to break the seal provided by pressure relief vent 200 may be desirable to perform a leak test on an instrument on which the pressure relief vent is mounted. The vent opening devices 216 included with pressure relief valve 200 are particularly adapted to be used to facilitate a leak test using a leak test fitting 600 shown in FIGS. 6 and 7. This leak test fitting 600 will first be described in the following paragraph, followed by a description of the use of the leak test fitting with pressure relief vent 200.

Figure 6:
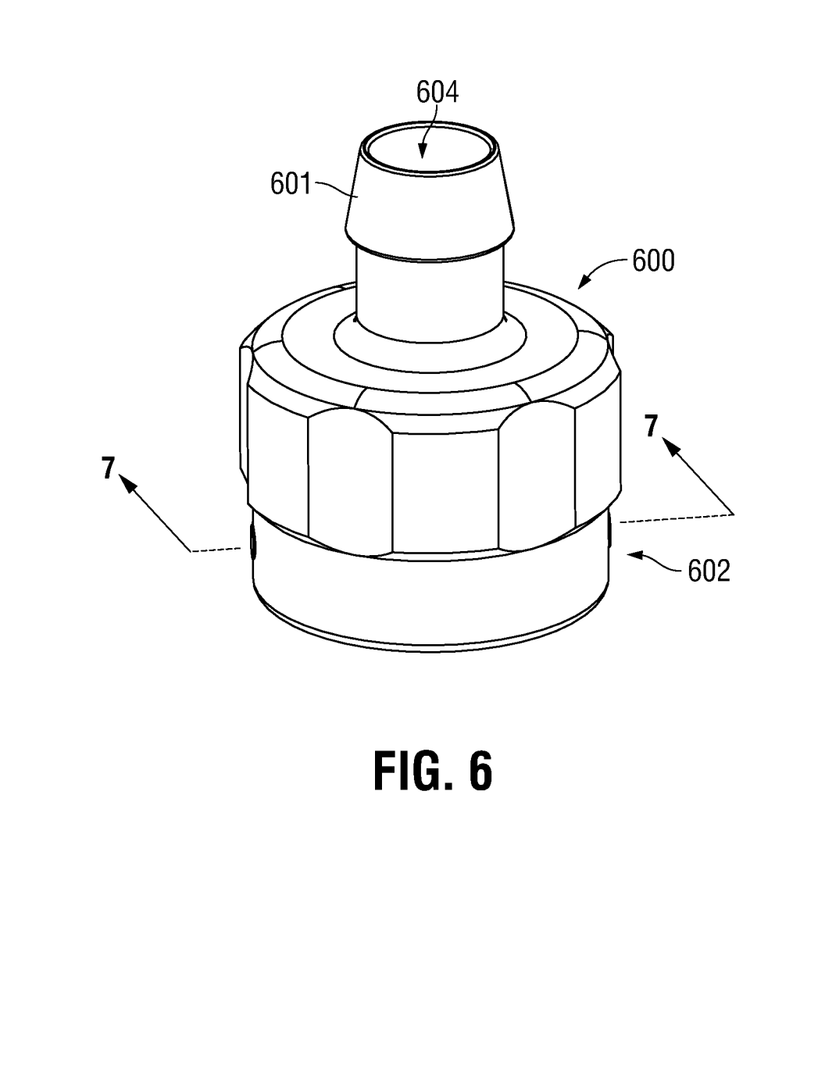
FIG. 6 is a perspective view of a leak test fitting adapted to be used with the pressure relief vent shown in FIGS. 2-5.
Figure 7:
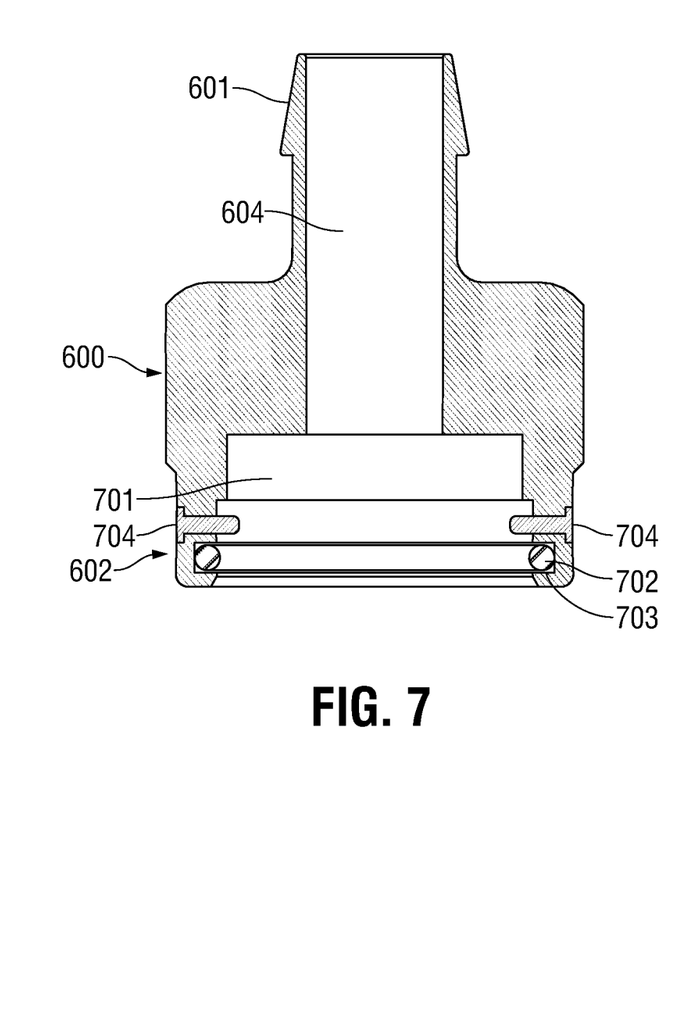
FIG. 7 is a view in section taken along line 7-7 in FIG. 6.

As shown in both FIGS. 6 and 7, leak test fitting 600 includes a barb connector 601 associated with a fitting passage 604. Barb connector 601 is at an opposite end of fitting 600 with respect to a proximal end 602 of the fitting. FIG. 7 shows that fitting passage 604 extends longitudinally through fitting 600 to a pressure relief vent receiving cavity 701 which is circular in shape in a plane perpendicular to the plane of the drawing. Cavity 701 is open at its lower end in the orientation of FIG. 7, corresponding to proximal end 602 of the fitting. An O-ring 702 is positioned at that lower end in an O-ring groove 703. The section view of FIG. 7 also shows that fitting 600 further includes pins 704 which project into cavity 701 on opposite sides of the fitting in this example.

The use of leak test fitting 600 to manually break the seal provided by pressure relief vent 200, may now be described with reference to FIGS. 4-7. With pressure relief vent 200 in the closed condition shown in FIG. 4, leak test fitting 600 is first positioned with its proximal end 602 aligned with and facing the distal end 211 of the pressure relief vent and with each pin 704 aligned with one of the entry slots 218 (shown in FIGS. 2 and 3). From this position, leak test fitting 600 and pressure relief vent 200 are brought together so that pressure relief vent distal end 211 is received in vent receiving cavity 701. Leak test fitting 700 and pressure relief vent 200 may be brought together in this fashion until pins 704 reach cutout bottom 217 shown in FIGS. 2-4. At this point with the pins 704 in contact with cutout bottom surface 217, O-ring 702 resides in contact with the exterior surface of upper housing 204 to provide a suitable seal between leak test fitting 600 and the upper housing. Also from this position with each pin 704 in contact with a respective cutout bottom surface 217, leak test fitting 600 may be rotated clockwise to move each pin 704 into contact with a respective ramp section 220 due to the relative size of each pin 704 and the narrowing distance between cutout bottom 217 and ramp section 220. This contact between each pin 704 and respective ramp section 220 on opposite lateral sides of pressure relief vent 200 as each pin moves along the ramp section allows the pins to function as lifting elements to ultimately force valve member 402 upwardly in the direction L1 shown in FIG. 5 until each pin 704 is received in the respective end part 221. Valve member 402 is lifted sufficiently to break the seal between O-ring 416 and surface 414 generally as shown in FIG. 5. With the leak test fitting 600 sealed to vent 200 around upper housing 204 and with the seal between O-ring 416 and surface 414 broken, pressure may then be applied through the leak test fitting (and through the pressure relief vent) into the interior volume of the instrument to which the pressure relief vent is connected so as to perform a leak test on the instrument. Once the leak test is complete, leak test fitting 600 may be rotated counterclockwise in this embodiment so as to align each pin 704 with the respective entry slot 218 and then the fitting may be removed from the distal end 211 of pressure relief vent 200. Of course, as each pin 704 moves along the respective ramp section 221 toward the respective entry slot, valve member 402 returns to the sealed position under the force provided by biasing device 410.

It will be noted that when the pressure relief arrangement in vent 200 is in the open condition, either in response to a positive pressure differential or in response to the installation of leak test fitting 600, it is possible for liquids to inadvertently enter the pressure relief vent. Because liquids may damage an instrument to which the pressure relief vent 200 is attached, it is desirable to include features in the vent to prevent liquid from passing through the vent to reach the instrument. Gas permeable membrane 422 shown in FIG. 4 is included in vent 200 to selectively block liquids while allowing gasses to flow there through. Thus any liquid which is inadvertently admitted into vent enclosure cavity 412 while the pressure relief arrangement is in the open condition is prevented from passing further to reach an instrument to which the vent may be secured via connector 214. Additionally or alternatively to membrane 422, clearances between the various components of pressure relief vent 200 may be selected to minimize the risk of liquids and debris from entering the device while the pressure relief arrangement is in the open condition.

Figure 8:
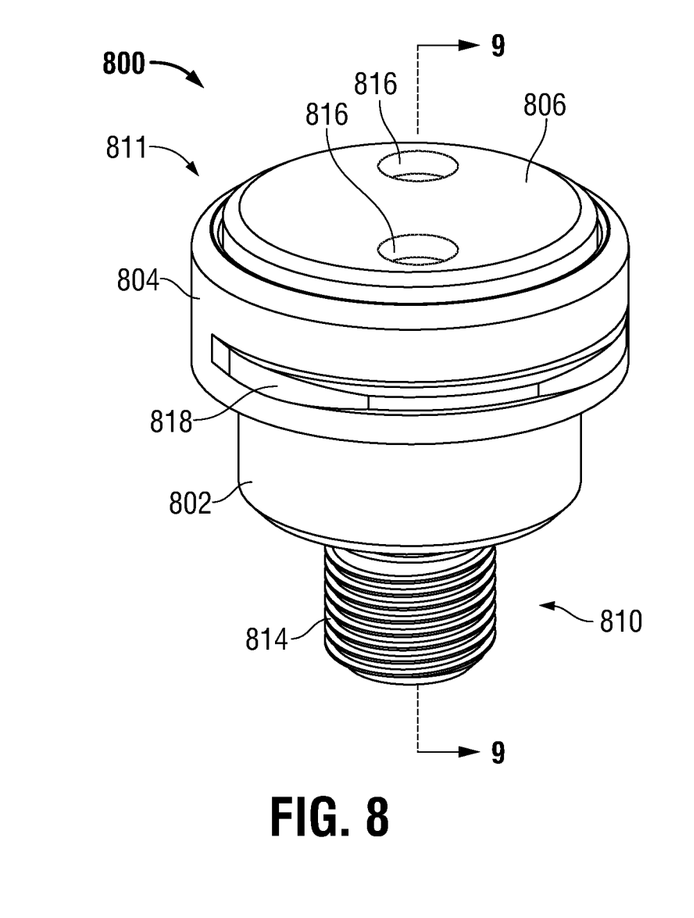
FIG. 8 is a perspective view of a pressure relief vent according to another embodiment of the present invention.
Figure 9:
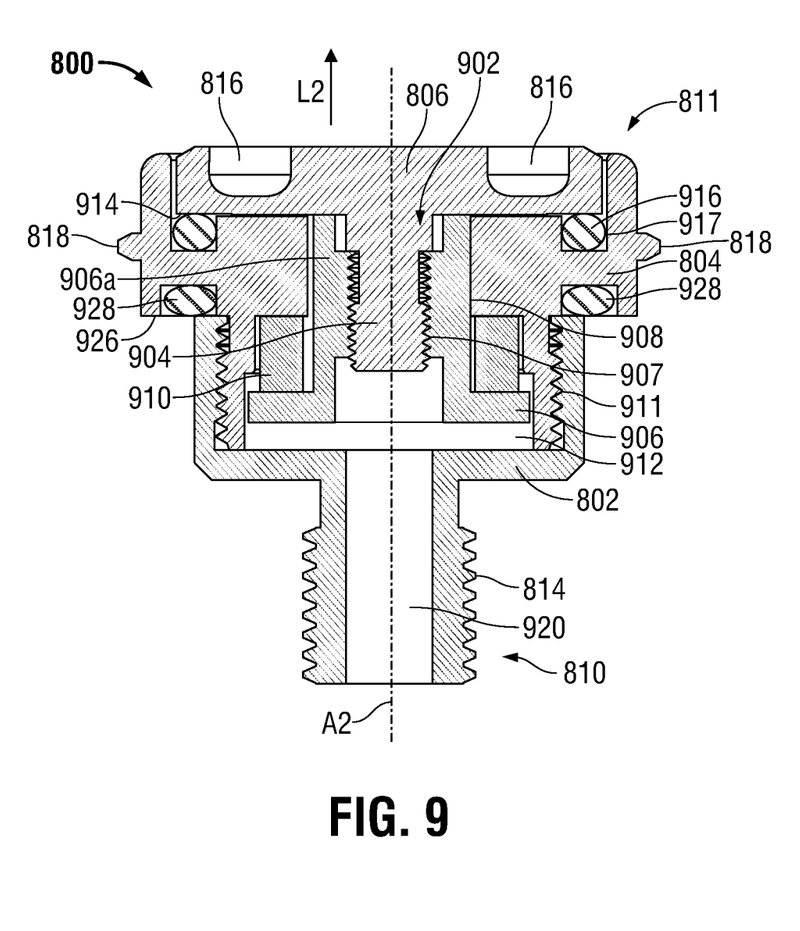
FIG. 9 is a view in section taken along line 9-9 in FIG. 8.

FIGS. 8 and 9 show another embodiment of a pressure relief vent according to the present invention. Similarly to pressure relief vent 200, pressure relief vent 800 includes a housing base 802, an upper housing 804, and a valve member with a cap section 806 which is visible in the perspective of FIG. 8. Pressure relief vent 800 has a proximal end generally shown at reference numeral 810 and a distal end generally shown at reference numeral 811. Cap section 806 is located at distal end 811, while a connector 814 is located at proximal end 801. In contrast to the J-slot type vent opening devices 216 included in pressure relief vent 200, pressure relief vent 800 includes a vent opening device which is not visible on the outside of the device and is thus not labeled in FIG. 8. However, receivers 816 and locking feature 818 are visible in FIG. 8 and are related to the vent opening device of vent 800 as will be apparent from the following discussion of FIGS. 10 and 11.

The section view of FIG. 9 shows valve member 902 which, in addition to cap section 806 includes a stem section 904 and a bottom plate 906. In this embodiment, bottom plate 906 includes a collar section 906a which is removably connected to stem section 904 through a preferably threaded connection 907. The bottom plate arrangement shown in FIG. 9 allows collar section 906a to be inserted through an aperture 908 of upper housing 804 with a biasing device 910 such as a suitable wave spring or other biasing device captured between bottom plate 906 and a bottom surface of upper housing 804, and then stem section 904 may be connected to collar section 906a through connection 907. With the bottom plate 906 connected and biasing device 910 captured, housing base 802 may then be connected to upper housing 804 through a threaded connection 911 so as to position both bottom plate 906 and biasing device 910 within a cavity 912 of the vent enclosure. Although not shown in FIG. 9, a gas permeable membrane may be captured within vent 800 similarly to membrane 422 shown in FIG. 4.

It should be noted here that as with the embodiment shown in FIG. 4 it is not necessary that bottom plate 906 be removably connected to the remainder of valve member 902. Rather, bottom plate 906 and stem section 904 may be adapted to be positioned as described and then welded or otherwise irremovably fixed in place capturing biasing device 910 against upper housing 804.

In the position shown in FIG. 9, biasing device 910 is operable to bias valve member 902 downwardly in the orientation of the figure (in the direction opposite direction L2 shown in FIG. 9). This bias forces a bottom surface 914 of cap section 806 against an upwardly facing O-ring 916 mounted in a groove 917 on upper housing 804. Contact between cap section bottom surface 914 and O-ring 916 produces a seal along the top of O-ring 916. This seal at O-ring 916 isolates the interior volume of the vent enclosure (in this case made up of the space between aperture 908 and collar section 906a, open space remaining in the cavity 912, and a passage 920 through housing base 802) from the atmosphere when pressure relief valve is connected to a sealed instrument via connector 814.

Pressure relief vent 800 may be connected to an instrument such as endoscope 100 similarly to the connection described above with reference to pressure relief vent 200.

In the case of pressure relief vent 800, O-ring 928 provides functions similarly to O-ring 428 described above in connection with FIG. 4. With pressure relief vent 800 in this operating position on a sealed instrument, the pressure within the interior volume of the instrument is applied through passage 920 and ultimately to valve member 902 (including cap section bottom surface 914). Once the pressure reaches a predetermined positive pressure differential between the interior volume of the vent enclosure and the atmosphere, the force applied to valve member 902 in the direction L2 in FIG. 9 is sufficient to overcome the force of biasing device 910 and lift valve member 902 in direction L2. It will be appreciated that this movement of valve member 902 separates surface 914 from O-ring 916 which allows gas to flow from the interior volume of the vent enclosure to the atmosphere. Gaps or channels between aperture 908 and the outer surface of collar section 906a and between the circumferential peripheral surface of cap section 806 and the inner surface of upper housing 904 facilitate gas flow to provide the desired pressure reduction. Once sufficient gas escapes so that the pressure differential is no longer above the predetermined value, biasing device 910 moves valve member 902 downwardly in the orientation of the figure to reestablish the seal with O-ring 916 and thereby return the vent and the connected instrument to its sealed state.

In the case of pressure relief vent 800, the pressure relief arrangement is represented by the combination of biasing device 910 together with valve member 902 movably mounted on upper housing 804. Although only the closed condition of this pressure relief arrangement is shown in the drawings, it will be appreciated that the open condition comprises the condition in which the valve member 902 is lifted relative to upper housing 804 so as to break the seal formed between cap section lower surface 914 and O-ring 916. As with pressure relief vent 200, the open condition corresponds to a compressed state of biasing device 910 and the closed condition corresponds to an expanded state of biasing device 910.

Figure 10:
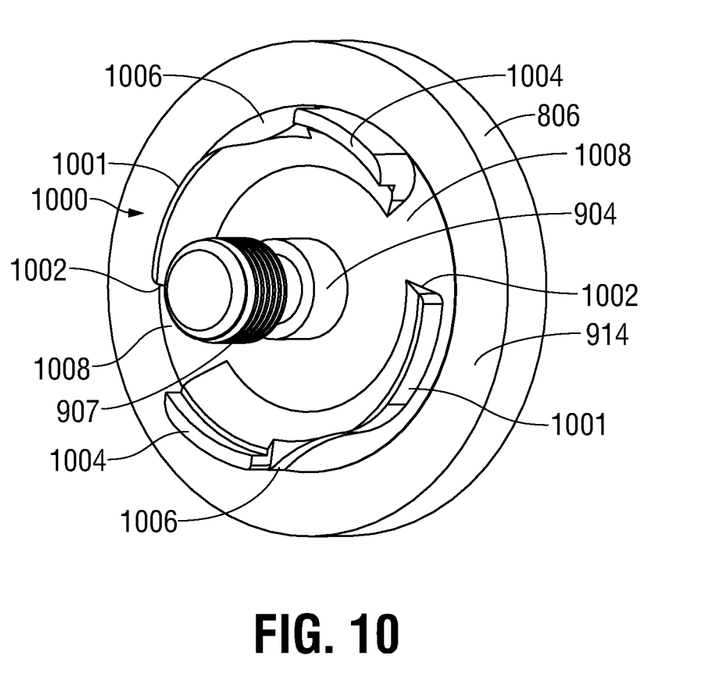
FIG. 10 is a perspective view of the valve member shown in FIG. 9.
Figure 11:
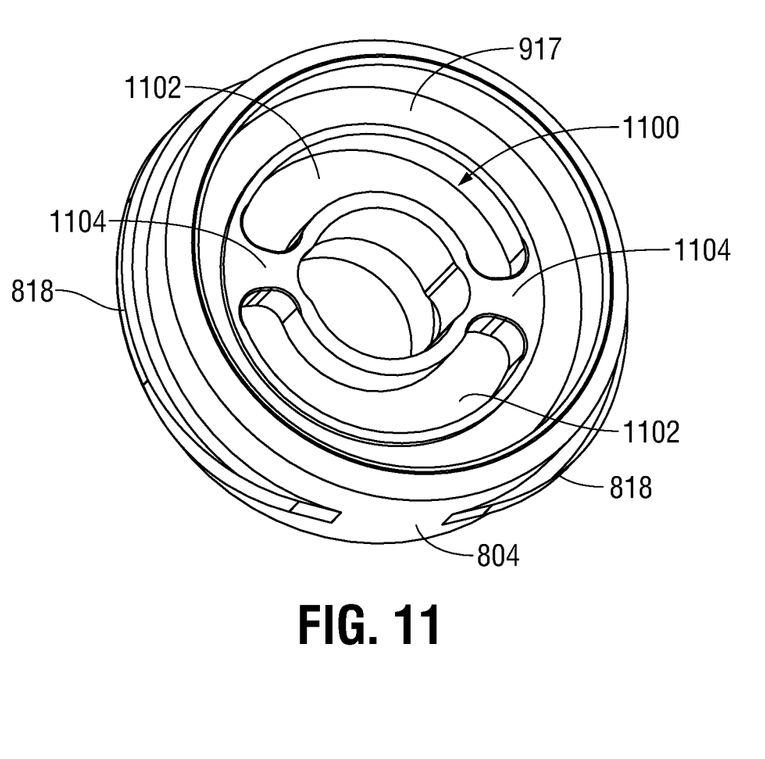
FIG. 11 is a perspective view of the upper housing shown in FIG. 9.

A vent opening arrangement associated with pressure relief vent 800 may now be described with reference to the perspective views of FIGS. 10 and 11. FIG. 10 shows a bottom side of valve member cap section 806, while FIG. 11 shows a top side of upper housing 804. These two sides, the bottom side of valve member cap section 806 and the top side of upper housing 804 face each other in the assembled vent 800 shown in FIG. 9. As is apparent from the perspective of FIG. 10, cap section 806 includes a first feature 1000 projecting from surface 914. This first feature 1000 together with a second feature 1100 shown in FIG. 11 form the vent opening arrangement which may be manually operated to selectively break the seal provided by pressure relief vent 800. First feature 1000 includes two separate arcuate elements 1001 each including a respective ramp section 1002, stop section 1004, and cutout section 1006. The two arcuate elements 1001 are separated by gaps 1008. Second feature 1100 includes two arcuate recesses 1102 separated by ridges 1104. The angular orientation of cap section 806 relative to upper housing 804 about the vent enclosure axis A2 in FIG. 9 determines the points at which ridges 1104 contact portions of feature 1000. In the assembled position shown in FIG. 9, each arcuate element 1001 is received in a different one of the recesses 1102 with the gaps 1008 aligned with ridges 1104. This angular position represents the closed condition of the pressure relief vent shown in FIG. 9. However, cap section 806 may be rotated relative to upper housing 804 so that ridges 1104 first contact the ramp sections 1002 and ultimately reach stop sections 1004. The movement of ridges 1104 across ramp sections 1002 lifts cap section 806 from upper housing 804 in the direction L2 in FIG. 9 sufficiently to separate the cap section surface 914 from O-ring 916 and break the seal provided by vent 800 in normal operation. Thus ridges 1104 function as lifting elements for ramp sections 1002. Continuing to rotate cap section 806 relative to upper housing 804 ultimately places each stop section 1004 in contact with a respective ridge 1104 to prevent further rotation. This angular orientation with each ridge 1104 aligned with a respective cutout section 1006 represents an open condition of the pressure relief vent, and the cutout sections serve as detents to resist inadvertent rotation back to the closed condition. The seal provided by pressure relief vent 800 may be reestablished by rotating cap section 806 back the opposite direction to ultimately place each gap 1008 on the valve member cap section 806 in alignment with a respective ridge 1104 on upper housing 804.

Figure 12:
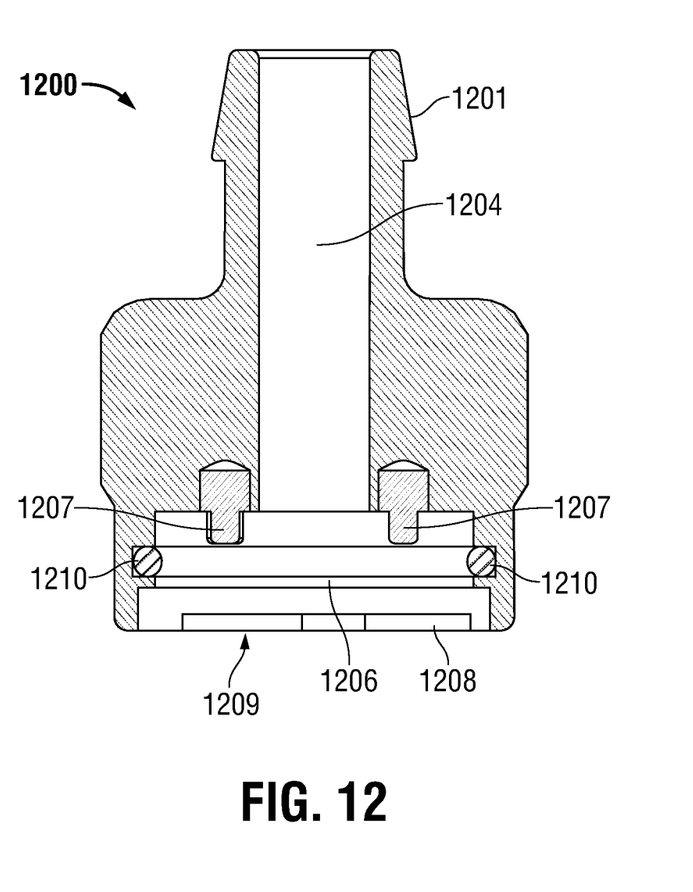
FIG. 12 is a view in section of a leak test fitting adapted for use with the pressure relief vent shown in FIGS. 8 and 9.

FIG. 12 shows a leak test fitting 1200 which may be used with pressure relief vent 800 to operate the vent opening arrangement described in the preceding paragraph and manually break the seal of the pressure relief vent to conduct a leak test for the instrument to which the vent is connected. Leak test fitting 1200 includes a barbed connector 1201 and a fitting passage 1204 extending through the barbed connector and to a vent receiving cavity 1206. Downwardly directed projections 1207 extend from the body of the leak test fitting into the vent receiving cavity 1206. A locking ridge 1208 is located at an opening 1209 to vent receiving cavity 1206 and an O-ring 1210 is located at an intermediate position between locking ridge 1208 and projections 1207.

In operation, and with pressure relief vent 800 in its closed condition shown in FIG. 9, leak test fitting 1200 is first rotated about its longitudinal axis until locking ridge 1208 aligns with the gaps between locking feature 818 (FIGS. 8 and 9) of the pressure relief vent. Once in this orientation, leak test fitting 1200 may be lowered over the distal end 811 of vent 800 until that distal end is received in vent receiving cavity 1206 and each projection 1207 enters a respective receiver 816 of valve member 902. When placed in this position over vent 800, O-ring 1210 forms a seal against the outer surface of upper housing 804 above locking feature 818 in the orientation of FIG. 9. With each projection 1207 thus received in a respective receiver 816, leak test fitting 1200 may be rotated about its longitudinal axis to thereby also rotate valve member 902 (including cap section 806) relative to upper housing 804. In particular, cap section 806 may be rotated from an initial orientation in which each gap 1008 aligns with a respective ridge 1104 to a second orientation in which each ridge 1104 aligns with a respective cutout section 1006. As cap section 806 is rotated from the initial orientation in which vent 800 is in its closed condition, contact between each ridge 1104 and a respective ramp section 1002 lifts cap section 806 and the remainder of valve member 902 with respect to upper housing 804 in direction L2 shown in FIG. 9. This relative movement between valve member 902 and upper housing 804 separates surface 914 shown in FIG. 9 from O-ring 916 to break the seal there between so that pressure may be applied through fitting 1200 to perform the desired leak test. It will be noted that as leak test fitting 1200 is rotated to break the vent seal, the locking ridge 1208 on either side of the fitting slides under a respective locking feature 818 of upper housing 804 to lock the leak test fitting and upper housing in place along axis A2. Once the leak test is complete, leak test fitting 1200 may be rotated in the opposite direction to rotate valve member 902 until cap section 806 returns to the sealed position relative to upper housing 804, and locking ridge 1208 disengages from locking feature 818. Leak test fitting 1200 may then be removed from the distal end 811 of the pressure relief vent 800.

Although both pressure relief vent 200 shown in FIGS. 2-5 and pressure relief vent 800 shown in FIGS. 8 and 9 include a respective vent opening arrangement, it will be appreciated that other embodiments of the invention may include no vent opening arrangement. These other embodiments of the invention may provide the desired pressure relief function, but may not facilitate opening the vent for leak testing or other purposes.

Figure 13:
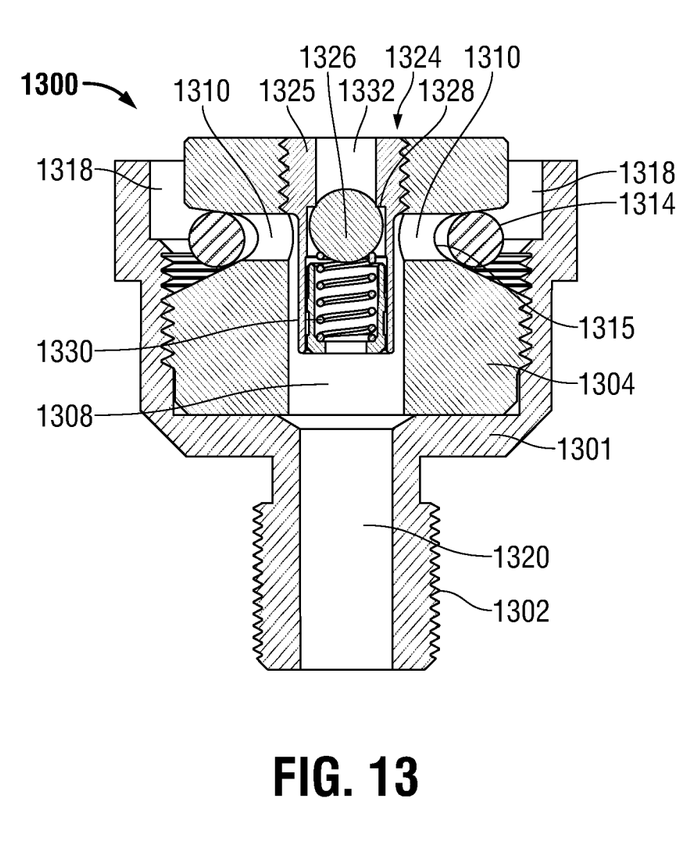
FIG. 13 is a view in section of a pressure relief vent according to another embodiment of the present invention.

FIG. 13 shows another embodiment of pressure of a pressure relief vent according to the invention. As with pressure relief vents 200 and 800, pressure relief vent 1300 shown in FIG. 13 may be connected to port 108 shown in FIG. 1 for use in connection with instrument 100.

Pressure relief vent 1300 includes a housing base 1301 having a connector 1302 corresponding to connectors 214 and 814 in vents 200 and 800, respectively. Housing base 1301 together with an upper housing 1304 define a vent enclosure having an interior volume made up of an upper housing passage 1308 and lateral channels 1310. The valve member in this embodiment comprises an O-ring 1314 received on an O-ring groove 1315 formed in upper housing 1304.

In operation, when a predefined positive pressure differential forms between the interior volume of pressure relief vent 1300, the pressure forces O-ring 1314 out of groove 1315 and allows gas to escape through channels 1310 and through the gap 1318 formed between upper housing 1304 and housing base 1301. Once the pressure differential is reduced to below the predefined level, the O-ring type valve member 1314 elastically returns to seat in the O-ring groove 1315 to reestablish the desired seal.

The embodiment shown in FIG. 13 includes a vent opening device 1324 that is separate and independent from O-ring/valve member 1314. In particular, vent opening device 1324 comprises a check valve including a valve body 1325, ball 1326, valve seat 1328, and biasing device 1330. Ball 1326 normally remains seated against seat 1328 under the biasing force provided by biasing device 1330, assisted by any positive pressure differential. However, the seal can be broken as desired such as to perform a leak test by inserting an element into the opening 1332 to press ball 1326 off of seat 1328. It is also possible to displace ball 1326 off of seat 1328 by applying sufficient gas pressure to opening 1332 to compress biasing device 1330 and overcome any opposing pressure within passage 1308. The strength of biasing device 1330 may be selected to allow displacement of ball 1326 at an appropriate pressure for performing a leak test.

Figure 14:
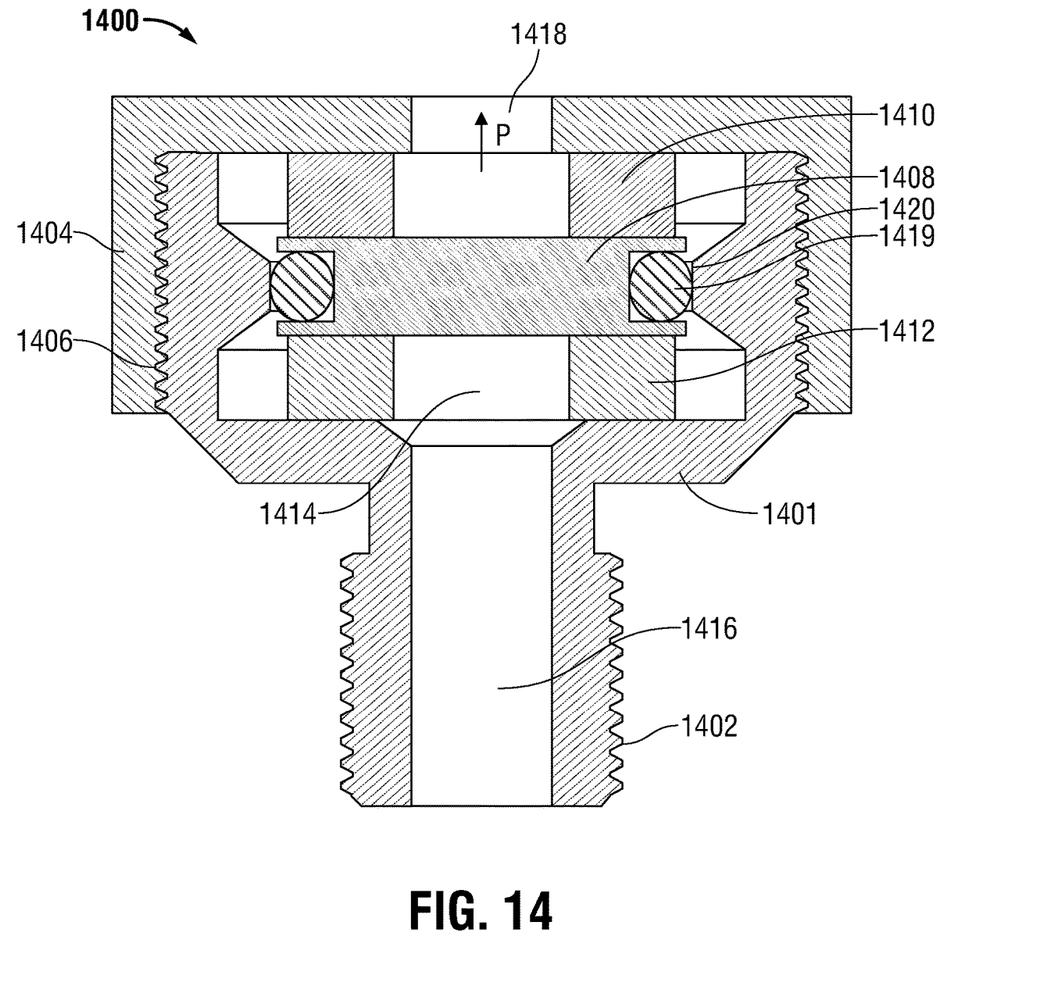
FIG. 14 is a view in section of a pressure relief vent according to a further embodiment of the present invention.

FIG. 14 shows another embodiment of a pressure relief valve according to the present invention. Pressure relief vent 1400 shown in FIG. 14 may be employed with an instrument such as endoscope 100 shown in FIG. 1 similarly to the previously described pressure relief vents 200, 800, and 1300.

Pressure relief vent 1400 includes a housing base 1401 having a connector 1402 which corresponds to connector 214 in FIG. 2 for example. An upper housing 1404 is connected to housing base 1401 through a suitable connector 1406 and captures a valve member 1408 together with biasing devices 1410 and 1412 in a cavity 1414 of housing base 1401. Housing base passage 1416 extends through connector 1402 and pressure relief passage 1418 is formed in upper housing 1404. An O-ring 1419 is mounted on valve member 1408 and forms a seal against a valve seat 1420 when the valve member is in the position shown in FIG. 14 balanced between the two biasing devices 1410 and 1412. In response to a predetermined positive pressure differential between the area below valve member 1408 and the atmosphere, the valve member moves upwardly in the orientation of FIG. 14 against the biasing force of biasing device 1410 to ultimately break the seal between O-ring 1419 and valve seat 1420 and allow gas to flow through in the direction shown by arrow P in FIG. 14. However, a higher atmospheric pressure applied to valve member 1408 through passage 1418 moves valve member 1408 against the force of biasing device 1412 downwardly in the orientation of the figure until the O-ring 1419 moves off of valve seat 1420 in the opposite direction. This allows gas to flow in the direction opposite to the direction indicated by arrow P in FIG. 14. Thus the embodiment shown in FIG. 14 allows automatic pressure relief both into and out of the interior volume of an instrument to which pressure relief vent 1400 is connected.

In any of the embodiments and implementations of a pressure relief vent according to the present invention, the pressure relief arrangement should be configured so that the vent moves to the open condition before a potentially damaging pressure differential is reached. For a positive pressure differential, that is, a differential where the pressure within the vent enclosure is higher than that the pressure of the atmosphere surrounding the pressure relief vent, the vent may be set to open at a pressure differential in the range from 0 mmHg to 760 mmHg, and more preferably in a range from 80 mmHg to 160 mmHg.

The various components of a pressure relief vent according to the present invention may be formed from any suitable material or combination of materials. The materials should be selected for compatibility with the instrument with which the vent is to be used, and the environments to which the instrument and vent may be subjected. For example, for pressure relief vents intended for use with medical endoscopes, the pressure relief vent components should be compatible with materials and conditions used in sterilizing procedures for such endoscopes.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

In the above descriptions and the following claims, terms such as top, bottom, upper, lower, and the like with reference to a given feature are intended only to identify a given feature and distinguish that feature from other features. Unless specifically stated otherwise, such terms are not intended to convey any spatial or temporal relationship for the feature relative to any other feature.

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

The invention claimed is:

1. A pressure control and leak test system for a medical instrument, comprising:
   an upper housing having a proximal end forming a cavity for fluid communication with an interior of the medical instrument and an aperture in fluid communication with the cavity through a distal end of the upper housing;
   a valve member having a proximal end including a stem within the aperture and a distal end including a cap section, the cap section having a proximal-facing end with a bottom surface and a distal-facing end with at least one receiver formed therein;
   a leak test fitting including at least one projection that engages the at least one receiver to rotate the cap section relative to the housing; and
   a vent opening arrangement including a first feature on the bottom surface of the cap section and a second feature on the distal end of the upper housing, the first feature in rotatable engagement with the second feature,
   wherein the valve member rotates relative to the housing causing the first feature and the second feature to seal the cap section with the housing in a first position and separate the cap section from the housing in a second position.

2. The system of claim 1, wherein a distal end of the aperture is blocked in the first position and at least partially open in the second position to allow fluid flow from the cavity through the aperture to between the cap section and the housing.

3. The system of claim 1, wherein the first feature includes an arcuate element and the second feature includes a ridge.

4. The system of claim 3, wherein the arcuate element further comprises a ramp projecting away from the bottom surface of the cap to engage with the ridge, the ramp at least partially engaged with the ridge in the second position and disengaged from the ridge in the first position.

5. The system of claim 4, further comprising an arcuate recess that receives the arcuate element in the first position.

6. The system of claim 5, further comprising a stop section at one end of the arcuate element that prevents the cap section from further rotation.

7. The system of claim 1, wherein the leak test fitting includes a fitting passage blocked from fluid communication with the aperture in the first position and in fluid communication with the aperture in the second position.

8. The system of claim 1, further comprising locking features on the upper housing that lock the leak test fitting to the upper housing in the second position.

9. The system of claim 8, wherein the locking feature comprises a gap, wherein a locking ridge of the leak test fitting aligns with the gap to allow the leak test fitting to engage the upper housing when the valve member is in the first position and engage the locking feature when the valve member is in the second position to lock the leak test fitting to the upper housing.

10. The system of claim 1, further comprising a biasing device engaged with the upper housing and the valve member to bias the cap section to the first position.

11. The system of claim 10, wherein the biasing device includes a biasing force configured to allow the cap section to move to the second position when a pressure differential between the cavity and atmospheric pressure exceeds a predetermined threshold.

12. The system of claim 1, further comprising a seal disposed between the bottom surface of the cap section and a groove in the distal end of the upper housing.

13. The system of claim 1, further comprising a seal disposed within a vent receiving cavity of the leak test fitting.

14. The system of claim 1, further comprising a threaded section on the proximal end of the upper housing for coupling to the medical instrument.

15. The system of claim 1, further comprising a threaded section on the proximal end of the upper housing for coupling to a housing base.

16. The system of claim 15, further comprising a connector on a proximal end of the housing base for coupling with the medical instrument.

17. The system of claim 10, wherein the biasing device includes a wave spring.

18. The system of claim 1, wherein the leak test fitting further comprises a barbed connector.

* * * * *